(12) United States Patent
Miller

(10) Patent No.: US 9,669,181 B2
(45) Date of Patent: Jun. 6, 2017

(54) BREATHING SYSTEMS

(71) Applicant: INTERSURGICAL AG, Vaduz (LI)

(72) Inventor: Andrew Neil Miller, Wokingham (GB)

(73) Assignee: Intersurgical AG, Vaduz (LI)

( * ) Notice: Subject to any disclaimer, the term of this patent is extended or adjusted under 35 U.S.C. 154(b) by 293 days.

(21) Appl. No.: 14/355,514

(22) PCT Filed: Nov. 1, 2012

(86) PCT No.: PCT/EP2012/071671
§ 371 (c)(1),
(2) Date: Apr. 30, 2014

(87) PCT Pub. No.: WO2013/064606
PCT Pub. Date: May 10, 2013

(65) Prior Publication Data
US 2014/0251322 A1    Sep. 11, 2014

(30) Foreign Application Priority Data

Nov. 1, 2011 (GB) .................................. 1118854.7

(51) Int. Cl.
*A61M 16/10* (2006.01)
*A61M 16/00* (2006.01)
(Continued)

(52) U.S. Cl.
CPC .... *A61M 16/0891* (2014.02); *A61M 16/0057* (2013.01); *A61M 16/01* (2013.01);
(Continued)

(58) Field of Classification Search
CPC ............................................. A61M 2205/3673
See application file for complete search history.

(56) References Cited

U.S. PATENT DOCUMENTS 4,451,435 A * 5/1984 Holter ................ B01D 53/0438
165/61
5,101,821 A    4/1992 Carie
(Continued)

FOREIGN PATENT DOCUMENTS

DE    10 2005 062 185 B3    7/2007
EP         2 335 760 A1    6/2011
(Continued)

OTHER PUBLICATIONS

International Preliminary Report on Patentability for corresponding PCT/EP2012/071671 (May 6, 2014).
(Continued)

*Primary Examiner* — (Jackie) Tan-Uyen T Ho
*Assistant Examiner* — Joseph D Boecker
(74) *Attorney, Agent, or Firm* — LeClairRyan, a Professional Corporation

(57) ABSTRACT

A heat exchange apparatus (26) for condensing water from a flow of respiratory gas is disclosed. The apparatus (26) comprises a first portion having an inlet (28) and a second portion having an outlet (30), the inlet (28) and outlet (30) being connectable to a breathing system (10) and the first and second portions being arranged in flow series, wherein the first portion comprises a condenser (64) and the second portion comprises a heater (64) downstream of the condenser for increasing the temperature of the respiratory gas flow prior to the outlet (30).

20 Claims, 7 Drawing Sheets

(51) Int. Cl.
*A61M 16/01* (2006.01)
*A61M 16/08* (2006.01)
*B01D 53/00* (2006.01)

(52) U.S. Cl.
CPC .... *A61M 16/0808* (2013.01); *A61M 16/1045* (2013.01); *A61M 16/0075* (2013.01); *A61M 2205/3673* (2013.01); *A61M 2206/14* (2013.01); *B01D 53/002* (2013.01)

(56) References Cited

U.S. PATENT DOCUMENTS

| | | | |
|---|---|---|---|
| 5,279,128 A * | 1/1994 | Tomatsu | F24F 3/1405 62/3.2 |
| 5,398,677 A | 3/1995 | Smith | |
| 5,722,393 A | 3/1998 | Bartel et al. | |
| 6,158,224 A * | 12/2000 | Hu | F24F 3/14 62/3.4 |
| 6,332,462 B1 * | 12/2001 | Krohn | A61M 16/1075 128/204.15 |
| 6,523,538 B1 * | 2/2003 | Wikefeldt | A61M 16/01 128/204.18 |
| 7,591,267 B2 | 9/2009 | Mashak et al. | |
| 7,779,840 B2 | 8/2010 | Acker et al. | |
| 8,439,036 B2 | 5/2013 | Winter et al. | |
| 8,439,037 B2 | 5/2013 | Winter et al. | |
| 8,469,030 B2 | 6/2013 | Winter et al. | |
| 8,469,031 B2 | 6/2013 | Winter et al. | |
| 9,205,221 B2 | 12/2015 | Winter et al. | |
| 2003/0199804 A1 * | 10/2003 | Ahlmen | A61M 16/009 604/6.09 |
| 2004/0237541 A1 * | 12/2004 | Murphy | B60H 1/00457 62/3.61 |
| 2007/0157929 A1 * | 7/2007 | Radomski | A61M 16/1075 128/204.18 |
| 2008/0009761 A1 | 1/2008 | Acker et al. | |
| 2009/0038615 A1 * | 2/2009 | Bradley | A61B 5/097 128/204.17 |
| 2010/0294279 A1 * | 11/2010 | Ionascu | A61F 7/007 128/203.26 |
| 2011/0030388 A1 * | 2/2011 | Johansson | F24F 3/14 62/3.4 |
| 2011/0126832 A1 | 6/2011 | Winter et al. | |
| 2011/0126835 A1 | 6/2011 | Winter et al. | |
| 2011/0133349 A1 * | 6/2011 | Weidmann | F24F 3/153 261/128 |
| 2011/0277541 A1 | 11/2011 | Kadle et al. | |
| 2013/0247905 A1 * | 9/2013 | Miller | A61M 16/0808 128/201.13 |
| 2014/0276176 A1 | 9/2014 | Winter | |
| 2016/0058969 A1 | 3/2016 | Winter et al. | |

FOREIGN PATENT DOCUMENTS

| | | |
|---|---|---|
| JP | 2006214696 A1 | 8/2006 |
| JP | 2006325751 A1 | 12/2006 |
| JP | 2010046107 A1 | 3/2010 |
| WO | 91/14476 | 10/1991 |
| WO | 0149351 A2 | 7/2001 |
| WO | 2007096649 A1 | 8/2007 |
| WO | 2011/058371 A1 | 5/2011 |
| WO | 2012072997 A1 | 6/2012 |

OTHER PUBLICATIONS

Search report for corresponding application GB 1118854.7, mailed Mar. 5, 2012.
International search report and written opinion for corresponding application No. PCT/EP2012/071671, mailed Feb. 6, 2013.

* cited by examiner

BREATHING SYSTEMS

This application is a national stage application under 35 U.S.C. §371 of PCT Application No. PCT/EP2012/071671, filed 1 Nov. 2012, which claims the priority benefit of Great Britain Application No. 1118854.7, filed 1 Nov. 2011.

This invention relates to breathing systems, and in particular to the management of water vapour and water condensate in breathing systems.

In a healthy person, the function of breathing is entirely spontaneous. The brain senses a build-up of carbon dioxide in the blood and immediately calls for more oxygen. This oxygen is taken into the body by spontaneous inspiration and carbon dioxide is removed in the passive exhalation phase of respiration. A healthy person generates a certain amount of humidity, which is used in the lung to stop the build-up of secretions.

The ability to breathe spontaneously may be lost for a number of reasons. Examples are as a result of surgical procedures (post-operatively), as a result of certain muscular disorders affecting the lung, or as a result of sedation by a clinician. Patients thus affected must be ventilated by mechanical means in order to achieve oxygenation and carbon dioxide removal.

When a patient is mechanically ventilated, it is essential that the humidity of the air is maintained at a sufficiently high level. This is conventionally achieved using a heat-moisture exchanger (HME) or a heated water bath humidifier. An HME retains the moisture in an exhaled breath and this moisture is sent back to the lung with the next inspiratory phase. In a water bath system, the inspiratory gas is passed through a heated water chamber and picks up humidity prior to entering the lung.

As humid respiratory gases travel through a breathing system, either in the inspiratory limb or the expiratory limb of a breathing circuit, a certain amount of water vapour will cool and start to condense, forming water droplets, which will start to build up, causing so-called "rain-out".

It is important to remove water condensate from the breathing system, so that it does not occlude the respiratory air flow or drain back into the patient's lungs thereby putting the patient at risk of drowning, or does not drain into the ventilator/anaesthetic equipment thus causing damage. If it is allowed to accumulate for a protracted period then due to its non-compressible nature the water can effectively block the breathing system.

The conventional arrangement for managing moisture in such a system is by the use of a device called a water trap. Such a device is generally located at the mid-point of the breathing system and positioned at the lowest point so that liquid will drain into it. Periodically, the accumulated condensate is emptied and the water trap replaced. However, this arrangement is not entirely satisfactory because water condensate still forms within the breathing system, and this water condensate may interfere with the operation of valves, sensors or ventilation machinery of the system. In particular, in conventional arrangements, it is common for water condensate to accumulate at the ventilator exhalation valve, for example. This can cause problems with flow measurement, resistance to flow, false triggering of alarms, and indeed occlusion of tubes.

It is also known to attempt to dehumidify the respiratory gases within a breathing circuit, for example before the respiratory gases are delivered back to the ventilator. One such arrangement is an exhalation breathing tube with an enclosing wall that allows the passage of water vapour therethrough, but prevents the passage of respiratory gases. However, these exhalation breathing tubes are expensive to manufacture, and typically remove only a portion of the water vapour content from the respiratory gases. If there remains a significant level of water vapour within the respiratory gases after dehumidification, it is a problem that the remaining water vapour can subsequently condense in other portions of the breathing system.

There has now been devised apparatus which overcomes or substantially mitigates at least some of the above-mentioned disadvantages associated with the prior art.

According to a first aspect of the invention, there is provided heat exchange apparatus for condensing water from a flow of respiratory gas, the apparatus comprising a first portion having an inlet and a second portion having an outlet, the inlet and outlet being connectable to a breathing system and the first and second portions being arranged in flow series, wherein the first portion comprises a condenser and the second portion comprises a heater downstream of the condenser for increasing the temperature of the respiratory gas flow prior to the outlet.

The heat exchange apparatus according to the invention is advantageous principally because the apparatus raises the temperature of the respiratory gas flow, downstream of the condenser, which raises the energy level of the respiratory gas flow prior to the gas passing through the outlet, thereby reducing the likelihood that any remaining vapour within the gas flow will condense out of the gas flow within another portion of the breathing system.

The heater may comprise a heater chamber, through which the respiratory gases flow, and the heater may be arranged to heat the respiratory gases within the heater chamber. The heater may be adapted so as to raise the temperature of the respiratory gas flow to a temperature greater than its dew point prior to passing through the outlet.

The heater may be adapted to heat the respiratory gases passively, but the heater is preferably adapted to heat the respiratory gases actively. The heater may be adapted to generate heat, which is transferred to the respiratory gas flow. The heater may produce a substantially constant amount of heat, such that there is no control of the heater, eg the heater is provided with a constant power supply. Alternatively, the apparatus may include a controller for the heater, for example to provide the respiratory gas flow with a predetermined temperature, or range of temperatures, at the outlet. This controller may control the power supplied to the heater, and may utilise one or more sensors for enabling feedback control.

The condenser may comprise a condensation chamber, through which the respiratory gases flow. The condenser may be arranged to reduce the temperature of the respiratory gas flow downstream of the inlet, and upstream of the heater. The condenser may be adapted to cool the respiratory gases within the condensation chamber. The condenser may be adapted to promote transfer of heat from the respiratory gases to the surroundings, ie to provide passive cooling, for example by providing a condensation chamber with an exterior of increased surface area, for a given volume, relative to a single flow passageway of substantially circular cross-section. Alternatively, or in addition, the condenser may include a cooler arranged to cool the respiratory gases actively. The cooler may be connectable to a power supply, and may provide transfer of heat from the condenser to the heater and/or a heat sink.

The temperature of the gas passing through the outlet may be greater than the temperature of the gas in the condenser. The condenser may be arranged to reduce the temperature of the respiratory gas flow to a temperature less than or equal to its dew point, and the heater may be adapted so as to raise the temperature of the respiratory gas flow to a temperature greater than its dew point.

The condensation chamber and the heater chamber may comprise different regions of a common chamber or enclosure. The condensation chamber and the heater chamber may be provided within a common housing. The common housing may be a heat exchange module, for example in the form of a cartridge, which may be of unitary construction. The condensation chamber and the heater chamber may comprise a plurality of heat conducting walls.

The apparatus may comprise a heat exchange medium arranged to transfer heat energy from the condenser to the heater. The heater and condenser may share a common heat exchange medium. Such an arrangement is advantageous in that the energy consumed by the apparatus in use is reduced by re-heating the gas flow using the heat energy removed from the flow by the condenser.

The apparatus may comprise a thermoelectric member. The condenser and/or heater may comprise a thermoelectric member. The thermoelectric member may be located in a single, unitary housing. The thermoelectric member may be arranged to provide thermal communication between the condenser and heater. The thermoelectric member may be connectable to a power source such that it is arranged to drive heat transfer from the condenser to the heater. The condenser may comprise a cold side of the thermoelectric member and the heater may comprise a hot side of the thermoelectric member.

The thermoelectric member may comprise a Peltier device.

Either of the first and/or second portions may comprise heat exchange members arranged to protrude into the path of the flow through the apparatus. The heat exchange members may comprise one or more upstanding walls arranged to define one or more flow passages through the first and/or second portions. The upstanding walls may take the form of baffles which may be arranged so as to define a tortuous flow path through the first and/or second portion. In one embodiment, the first and second portions are defined by a chamber with at least one wall being formed with inwardly projecting members, for example at least one wall may include corrugated portions.

One of the condensation chamber and the heater chamber may have a volume which is larger than that of other. A length, width or depth dimension of one of the chambers may be greater than that of the other chamber. Accordingly the time taken for the flow to pass through one of the chambers may be greater than the time taken for the flow to pass through the other chamber. One of the chambers may have a heat exchange surface area exposed to the flow there-through which is greater than the heat exchange surface area of the other chamber. Alternatively, the volume, dimensions and/or flow period may be equal for the chambers.

Even where the apparatus comprises a heat exchange medium or thermoelectric member for transferring heat from the condenser to the heater, the apparatus may produce excess heat. The apparatus may include a heat sink for removing excess heat from the apparatus. The heat sink may be external of any condenser and/or heater chamber of the apparatus. The heat sink may comprise a plurality of heat exchange elements, which may be exposed to ambient air. The heat sink may comprise a fan arranged to create a flow of ambient air over the heat exchange elements. The heat sink may be arranged to dissipate heat energy from the system to ambient air.

According to one embodiment, the apparatus may further comprise a base unit adapted to aid removal of heat energy from the condenser and/or aid provision of heat energy to the heater. The base unit may comprise the heat exchange medium or thermoelectric element described above. The first and/or second portions may be releasably engageable with the base unit. The first and second portions may comprise a heat exchange module. The heat exchange module may be releasably engageable with the base unit such that the base unit may be reusable, whereas the heat exchange module may be replaceable and/or disposable.

This apparatus is advantageous because the apparatus condenses water from respiratory gases within a heat exchange component, which enables the water to be removed from the breathing system. The present invention therefore reduces the risk that water condensate will form in the breathing system that will interfere with the operation of valves, sensors or ventilation machinery of the system. Also the base unit heats the gas flow immediately downstream of the condensation chamber so as to allow the temperature of the gas flow to be raised before exiting the apparatus.

Furthermore, the modular, replaceable nature of the heat exchange component allows the base unit to be configured to avoid contact with the respiratory gases or water condensate, and hence enables the base unit to be a reusable component, with the heat exchange component being a disposable component. This is advantageous as it means the base unit can be used safely and cost effectively with multiple patients by replacing the heat exchange component between patients. In addition, the present invention is less expensive than arrangements in which the entire apparatus is disposable.

Indeed, where the apparatus and/or base unit include means for actively cooling the respiratory gases conveyed through the condensation chamber, in use, for example by transferring heat from the walls of the heat exchange component, the replaceable nature of the heat exchange component provides particular cost benefits. In particular, the heat transfer device, eg a Peltier device, is preferably provided in the base unit of the present invention, and hence may be reused. Furthermore, the heat exchange component of the present invention is preferably of simple construction, eg formed from two moulded parts, and hence inexpensive to manufacture.

The inlet and outlet of the heat exchange apparatus preferably each have the form of a conventional tubular connector for connection to other components of breathing systems. The inlet and outlet ports may be provided on a common wall of a housing for the first and second portions. The inlet and outlet may face in substantially the same direction.

The apparatus may comprise an arrangement for collecting the liquid condensate for removal. The first portion may comprise a liquid outlet or drainage port. The inlet and outlet are preferably spaced from the drainage port. The drainage port is preferably formed in a lower wall of the first portion. The inlet may be provided in an upper wall of the first portion. Such an arrangement serves to prevent the flow of condensate into the connected breathing system.

The apparatus may comprise a liquid receptacle which is removably attachable to the drainage port. The drainage port or receptacle may comprise a valve, for example to prevent escape of gas through the port. A float valve, or similar, may be provided to allow selective escape of condensate from the first portion without allowing patient gases to escape.

The base unit may comprise a power supply for the heat exchange device.

The apparatus according to the invention is adapted to condense liquid such as water from respiratory gases. The apparatus may include an arrangement for collection and/or removal of the water condensate from the breathing system.

The condensation and/or heating chamber preferably has an increased interior surface area relative to a single flow passageway having a generally circular cross-section. The condensation and/or heater chamber preferably comprises a plurality of flow passageways, which are each adapted to convey respiratory gases, in use. Such an arrangement may provide an increased surface area for heat transfer to/from the gas flow therethrough. For example, the ratio of the internal width of the flow passage to the internal depth of the flow passage is preferably at least 1:2, more preferably at least 1:7, and most preferably about 1:10 or more.

The heat exchange component is preferably a disposable component, which is preferably formed of plastics material, but may be formed of metal, or at least include metal portions to aid conduction to and/or from the heat exchange component. The heat exchange component preferably forms a closed system, relative to the base unit, such that there is no contact between the respiratory gases of the breathing system and the base unit.

The heat exchange component and the base unit preferably include one or more formations that cooperate to mount the heat exchange component relative to the base unit. The heat exchange component and base unit may comprise correspondingly shaped formations. The cooperating formations may comprise heat exchange members or elements, such as one or more protruding wall portions and one or more recesses arranged to receive the protruding walls.

The apparatus and/or heat exchange component of the above-defined aspects is connectable to a breathing system, such that respiratory gases are conveyed through the first and second portions, in use. Hence, according to a further aspect of the invention, there is provided a breathing system comprising apparatus as described above.

The breathing system is preferably a breathing circuit, which will typically include at least a ventilator or an anesthesia machine, and an inspiratory limb. However, the present invention is particularly advantageous for removing water from exhaled gases, and hence the breathing circuit preferably also includes an expiratory limb, and the apparatus according to the invention is preferably connected within the breathing circuit, such that it forms part of that expiratory limb. In particular, the expiratory limb preferably comprises at least two breathing tubes, with the heat exchange apparatus connected between those breathing tubes, preferably at the lowest point of the expiratory limb.

The breathing system may be an anaesthetic circuit, ie a breathing circuit for providing anaesthetic gases to a patient. The anaesthetic circuit may include one or more sensors. Sensors are generally provided within anaesthetic circuits in order to monitor relevant parameters. Condensate from breathing gases can interfere with the sensors. It is therefore a further advantage of the invention that the extent to which condensate within the anaesthesia circuit interferes with the sensors may be reduced.

The breathing system may contain a carbon dioxide absorber. As the efficiency of some types of carbon dioxide absorber may be adversely affected by a reduction in the humidity of the gas upon which the absorber operates, the heat exchange apparatus may be adapted such that the humidity of the respiratory gas flow leaving the heat exchange apparatus is sufficient to allow the carbon dioxide absorber in the respiratory circuit to function effectively. The heat exchange apparatus may therefore be provided with a controller for controlling the efficiency of the heat exchange apparatus, for example by controlling the power supplied to the condenser and/or heater. This may simply take the form of a reduced power setting for use in anaesthetic circuit. Controlling the efficiency of the heat exchange apparatus allows the user to control the humidity of the gas. Therefore, an appropriate efficiency can be selected which causes the gas leaving the heat exchange apparatus to have a humidity at which the carbon dioxide absorber can function effectively. The efficiency may be controlled by changing the amount of power supplied to the condenser.

It is also noted that the apparatus according to the invention described above may be adapted for use as a heat and moisture exchange (HME) device, which would typically be located at the patient end of a breathing circuit. In particular, the feature that the respiratory gases are conveyed through a heat exchange component that is releasably engageable with the base unit, such that the heat exchange component is replaceable, would be particularly advantageous in this arrangement. This may enable the base unit to be arranged not to come into contact with the respiratory gases or water condensate, and hence enable the base unit to be a reusable component, with the heat exchange component being a disposable component. This is advantageous as it means the apparatus can be used safely and cost effectively with multiple patients by replacing the heat exchange component between patients. In addition, the present invention is less expensive than arrangements in which the entire apparatus is disposable.

Where the apparatus is adapted for use as a heat and moisture exchange (HME) device, the apparatus may be adapted to remove water and heat from expiratory gases in an expiratory passageway of the apparatus, and transfer that heat and water to inspiratory gases in an inspiratory passageway of the apparatus. The replaceable nature of the heat exchange component would reduce the cost of this apparatus significantly relative to other HME devices that utilise thermoelectric devices, such as Peltier devices, because the base unit may be reusable and the heat exchange component may be of simple construction.

Hence, according to a further aspect of the invention, there is provided a heat and moisture exchange device comprising a heat exchange component having an inlet, an outlet and a condensation chamber and/or a heater chamber, the inlet and outlet being connectable to a breathing system, such that respiratory gases are conveyed through the condensation chamber, in use, and a base unit adapted to aid removal of heat from the walls of the condensation chamber and/or aid provision of heat energy to the heater chamber, wherein the heat exchange component is releasably engageable with the base unit, such that the heat exchange component is replaceable.

According to a further aspect of the invention, there is provided a heat exchange component for use with a heat and moisture exchange device, the heat exchange component having an inlet, an outlet and a condensation chamber and/or a heater chamber, the inlet and outlet being connectable to a breathing system, such that respiratory gases are conveyed through the condensation chamber and/or the heater chamber, in use, wherein the heat exchange component is releasably engageable with a base unit adapted to aid removal of heat from the walls of the condensation chamber and/or aid provision of heat energy to the heater chamber.

According to a further aspect of the invention, there is provided a base unit for use with a heat exchange component to form a heat and moisture exchange device, the base unit being adapted to releasably engage the heat exchange component, and the base unit being adapted to aid removal of heat from the walls of the condensation chamber and/or aid provision of heat energy to the heater chamber.

The heat exchange component of this aspect of the invention may have only a condensation chamber, and hence define an expiratory flow path only, or may have only a heater chamber, and hence define an inspiratory flow path only. Indeed, the apparatus may be provided with two heat exchange components, one defining the expiratory flow path, and one defining the inspiratory flow path. Alternatively, the heat exchange component may have both a condensation chamber and a heater chamber, and hence may define both an expiratory flow path and an inspiratory flow path. In all of these arrangements, however, the heat and moisture exchange device preferably includes an arrangement for transferring water condensed from the expiratory gases in the condensation chamber to the heater chamber for humidifying the inspiratory gases. This transfer arrangement may take the form of a suitable conduit.

Any of the preferable features described above in relation to any one aspect of the invention may be applied to any further aspect of the invention wherever practicable.

Workable embodiments of the invention will now be described in greater detail, by way of illustration only, with reference to the accompanying drawings, of which;

The present invention may be considered to derive from the general premise that, instead of increasing the dehumidification of a gas flow to avoid condensation in unwanted regions of a respiratory system, it is possible to heat, or re-heat, the gas flow, typically immediately after dehumidification, such that any water vapour within the downstream gas flow is less likely to condense. Additionally or alternatively, the invention may be considered to derive from the premise that it is possible to advantageously re-use heat energy removed from the gas flow during dehumidification.

Figure 1:
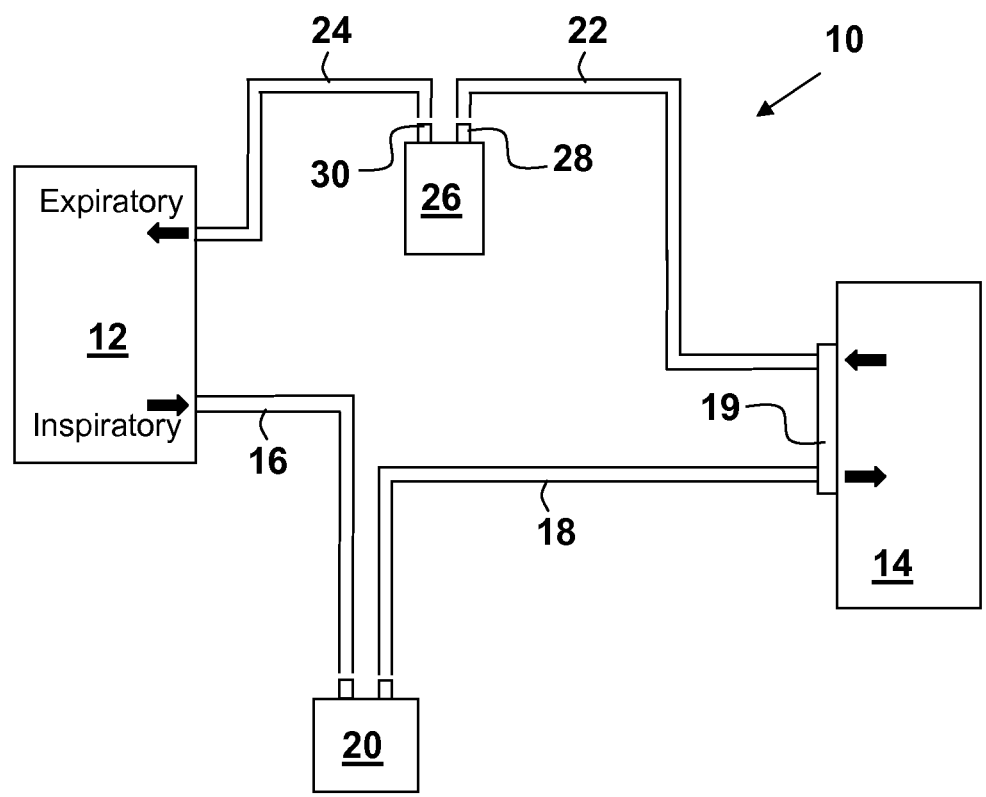
FIG. 1 is a schematic diagram of a respiratory circuit including the apparatus according to the invention.

FIG. 1 is a schematic diagram of an exemplary breathing circuit 10 including dehumidifying apparatus according to the invention. The breathing circuit comprises a ventilator 12, an inspiratory limb for delivering respiratory gases to a patient 14 for inhalation, and an expiratory limb for transporting exhaled respiratory gases back to the ventilator 12. The inspiratory limb comprises two breathing tubes 16, 18 and a humidifier 20 between the two breathing tubes 16, 18 for humidifying the respiratory gases before inhalation by the patient 14. The breathing tube 18 disposed between the humidifier 20 and the patient 14 is typically heated, in order to maintain the temperature and humidity of the respiratory gases at a desired level for inhalation.

The expiratory limb comprises two breathing tubes 22, 24 and the dehumidifying apparatus 26 of the invention connected between the two breathing tubes 22, 24 for removing water vapour from the exhaled respiratory gases before those respiratory gases are returned to the ventilator 12. Removal of water vapour from the exhaled respiratory gases by the dehumidifying apparatus 26 reduces the risk of damage being caused to the ventilator 12 by the water vapour, and also reduces the amount of condensation that occurs within the breathing tubes of the expiratory limb, which may restrict or occlude the flow passageways of the breathing tubes.

A conventional patient interface 19 provides the necessary connections between the patient's airway and the tubes 18 and 22.

In use, when the patient 14 exhales, expired air is carried along the first breathing tube 22 and enters the dehumidifying apparatus 26 via an air inlet port 28. Moisture is removed from the gas flow as it passes through the body of the dehumidifying apparatus 26 and the gas flow exits the apparatus via outlet port 30 en route to the ventilator 12 via tube 24.

The skilled person will appreciate that other conventional valves and connectors may be present in the breathing system, such as, for example, an expiratory valve at the connection between the ventilator 12 and the tube 24 and/or a connector between the patient interface 19 and either or both of the tubes 18, 22. The details of those devices and any other conventional parts of the breathing circuit are omitted for brevity.

FIGS. 2 to 7 each show a first embodiment of dehumidification apparatus according to the invention, which is generally designated 26. The apparatus comprises a base unit 32 and a removable/replaceable cartridge 34. The cartridge 34 may otherwise be considered to constitute a gas flow vessel or flow chamber.

The cartridge 34 generally comprises a thin-walled, hollow member shaped to define an internal gas-filled void. The cartridge 34 provides a gas-tight chamber with the exception of the ports 28, 30 and 36. The ports 28 and 30 provide respective inlet and outlet ports for the flow of respiratory gas into and from the cartridge 34 in use. The port 36 is a liquid drainage port, the details of which will be described below.

Figure 2:
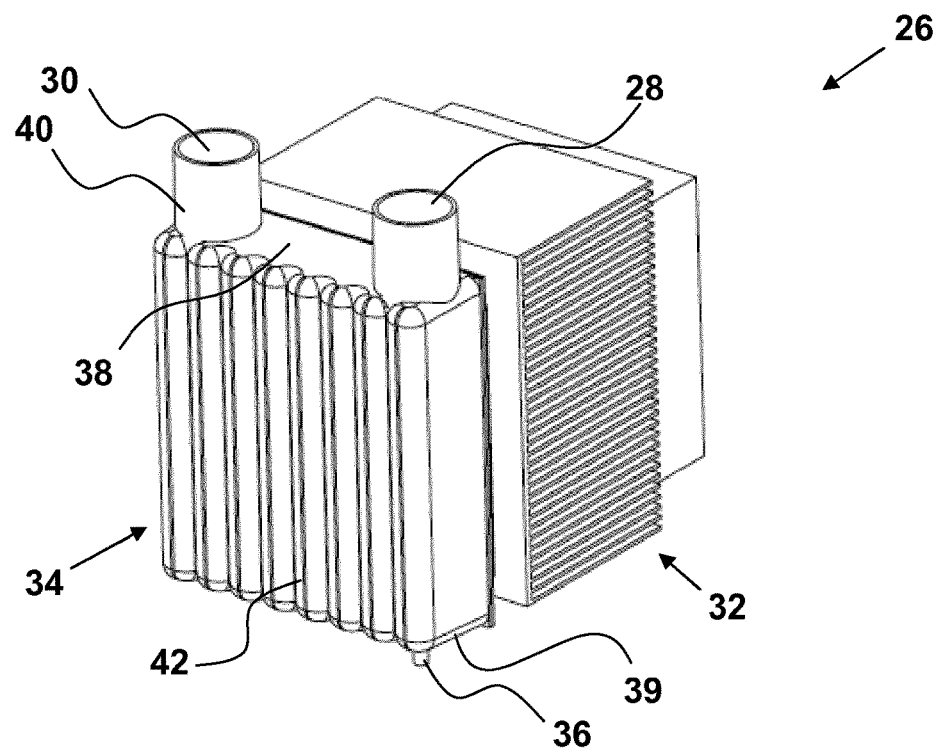
FIG. 2 is a three-dimensional view from the front of a first embodiment of heat exchange apparatus according to the invention.
Figure 3:
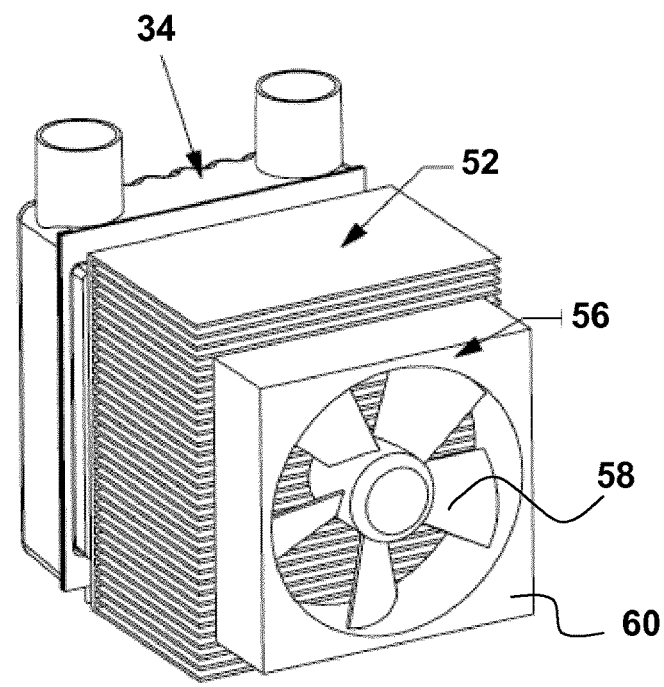
FIG. 3 is a three-dimensional view from the rear of the heat exchange apparatus of FIG. 2.

The ports 28 and 30 are provided in a common outer wall 38 of the cartridge 34, which wall in use is typically arranged to provide an upper, or upwardly facing, wall of the cartridge 34. An opposing, lower wall 39 is provided, which constitutes the base of the cartridge 34 in an in-use orientation as shown in FIGS. 2 and 3. The ports 28 and 30 are provided with respective upstanding connector formations 40, which each take the form of an annular wall depending from the wall 38. The connectors 40 are of conventional size to closely and securely fit with the ends of breathing tubes 22 and 24 as shown in FIG. 1. When connected in this manner, the internal chamber of the cartridge 34 is sealed from ambient air and/or any external devices such that the interior of the cartridge 34 forms a part of the closed flow path of the respiratory system shown in FIG. 1.

The cartridge 34 is preferably formed of a suitably rigid plastic material, for example by injection moulding.

The cartridge 34 is generally rectangular in plan and has a substantially continuous front wall 42, which faces away from the base unit 32 when the cartridge is mounted thereon for use.

The opposing (rear) wall 44 of the cartridge, which faces the base unit 32 has a series of longitudinal slots or recesses therein. In this regard the wall structure of the cartridge 34 is shaped to provide a plurality of wall projections 48 which protrude from the rear wall 44 into the internal volume of the cartridge 34. Those projections 48 thus reduce or 'eat into' the internal volume of the cartridge 34. The wall projections 48 can be seen from above in FIG. 6 through the ports 28, 30.

The flow channels thus present a large internal wall surface area to the flow passing through the cartridge so as to increase the area available for heat transfer to/from the flow in use.

Figure 5:
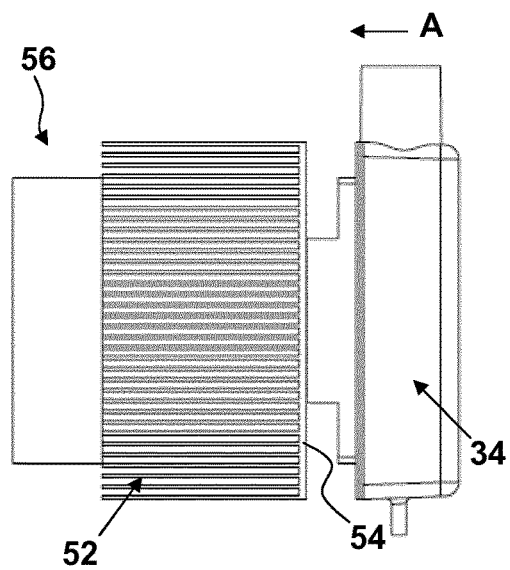
FIG. 5 is a side view of the apparatus of FIG. 2.
Figure 6:
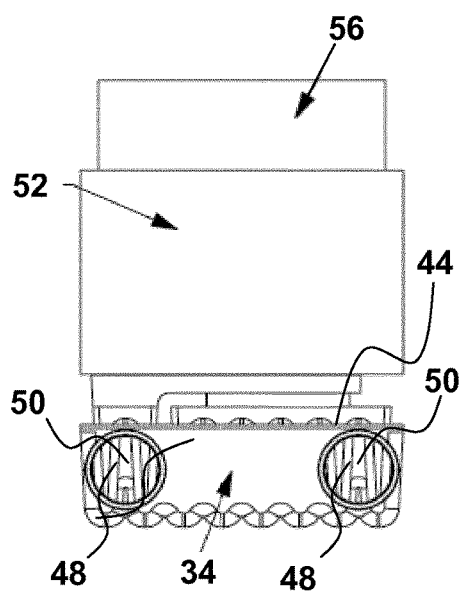
FIG. 6 is an above view of the apparatus of FIG. 2.

Turning now to FIGS. 3 and 5, there are shown further details of the base unit 32 which comprises a heat-dissipating structure comprising a series of generally planar fins 52 depending from a support plate 54. The fins 52 are generally upstanding from the support plate, typically perpendicularly thereto. The fins 52 are spaced along the plate 54 and generally parallel in alignment such that each fin 52 is spaced from an adjacent fin 52 by an air-gap.

Each fin 52 is supported only along one edge by the plate 54 such that the further sides of the heat-dissipating structure, comprising of the aligned edges of the fins, are open. The fins and support plate are formed of metal as a unitary structure and may be unitarily formed.

A fan unit 56 is mounted on the rear side of the heat dissipating structure. The rear side is the open side of the structure which opposes, or faces away from, the support plate 54. The fan unit 56 comprises a fan 58 arranged for rotation within a fan housing 60, by which the fan unit 56 is attached to the heat dissipating structure. The fan unit 56 is electrically powered to drive the fan in rotation in a direction which draws ambient air through the fins and expels air to the surroundings, typically in a direction away from the apparatus 26. In the orientation shown in FIG. 3, the fan 56 rotates anti-clockwise.

Figure 4:
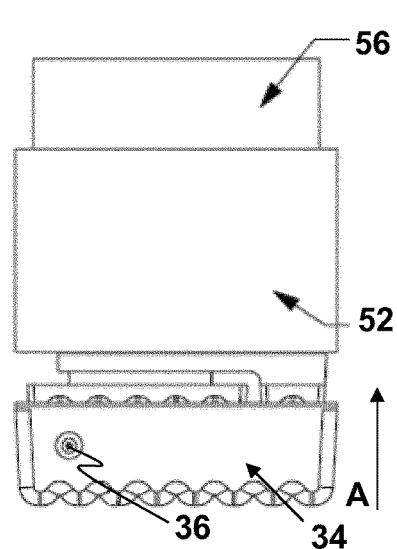
FIG. 4 is a below view of the apparatus of FIG. 2.
Figure 7:
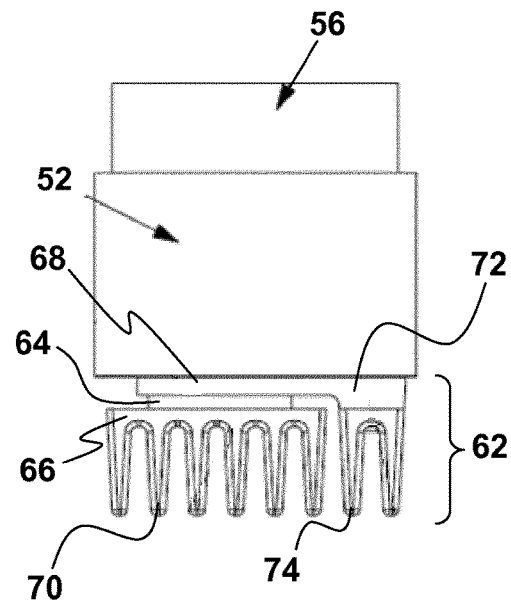
FIG. 7 is a below view of the apparatus of FIG. 2 with the cartridge removed.

Turning now to FIGS. 4 and 7, there are shown respective views of the base unit 32 with and without the cartridge 34 attached. A heat transfer structure 62 is provided between the heat dissipating structure and the cartridge 34. The heat transfer structure depends from the support plate 54 in a direction facing away from the fan unit 56.

The heat transfer structure 62 comprises a heat transfer element or heat pump 64, which is arranged between thermal conductors 66 and 68. In this embodiment, the heat pump 64 is a thermoelectric heating/cooling device, which takes the form of a Peltier device. Such a device may otherwise be described as a solid-state active heat pump. The Peltier device has opposing major faces which are plate-like conductors and a plurality of thermoelectric elements therebetween (not shown), which are arranged electrically in series but thermally in parallel between the opposing plate conductors. Accordingly the supply of electric power to the device drives a temperature difference between the conductor plates such that a first plate conductor comprises a cold side of the device and the opposing conductor comprises a hot side of the device.

The cold side of the Peltier device 64 is connected to the conductor arrangement 66. This conductor arrangement comprises a plurality of projections 70 depending away from the Peltier device. The projections 70 are spaced in a series or configuration which corresponds to the recesses 46 in the rear wall of the cartridge. The projections 70 are elongate in form and upstanding akin to fins or finger-like formations which are shaped to form a close fit with the wall projections of the cartridge 34 and thereby form a good thermal contact therewith. The projections 70 depend from a generally planar backing portion which forms a thermal contact over the area of the cold side of the Peltier device for heat transfer therewith.

The hot side of the Peltier device 64 is connected to conductor formation 68, which comprises a relatively thin walled or planar body 72 which is sandwiched between the hot side of the Peltier device 64 and the back/support plate 54 of the heat dissipating structure. Towards an edge of the body 72 (i.e. towards the right hand edge as shown in FIG. 7), there are provided further upstanding projections 74. The projections 74 project outwardly from the body 72 in the same direction as the projections 70. The projections 74 in this embodiment are shaped and spaced in a manner which corresponds to that of the projections 74. Hence the projection 70 and 74 are substantially the same shape.

However, it can be seen that there are fewer of the projections 74 than there are of projections 70. In this embodiment, the ratio between the projections 70 and 74 is 3:1, such that there are six 'cold' projections 70 and only two 'hot' projections 74. However different ratios and/or numbers of projections 70,74 may be provided as necessary. The combined array of the projections 70 and 74 is arranged for insertion into the recesses 46 in the cartridge, such that some of the recesses are filled by the projections 70 and other recesses are filled by projections 74. It is notable that the projections 70 are grouped, as are the projections 74 such that those different types of projections are not interspersed.

The cartridge 34 is mounted for use to the base unit 32 by aligning the projections 70, 74 with the recesses in the rear wall of the cartridge 34 and then moving the cartridge 34 rearwardly (in the direction of arrow A in FIGS. 4 and 5) such that the projections slot into the recesses. In alternative embodiments, the cartridge 34 could be slid over the projections 70,74 in the longitudinal direction. In either embodiment, the cartridge 34 and/or projections 70,74 could be provided with one alignment grooves or ridges to ensure a close/tight fitment between the cartridge 34 and base unit 32.

In readiness for use, the ports 28 and 30 are connected to the respective tubes 22 and 24 in the respiratory system as shown in FIG. 1. The base unit 32 is also connected to a power supply, which typically comprises a connection to a mains power supply by a suitable lead (not shown), such that electrical power is supplied to the Peltier device 64 and fan unit 56. The supply of power to the Peltier device 64 drives a temperature difference between the opposing sides of the device by thermoelectric effect, thereby cooling the projections 70, whilst heating projections 74.

Thus, in use, when a cartridge 34 is located on the device such that it is in thermal conductive contact with the projections 70,74, a first plurality of the internal wall portions 48 are cooled by projections 70, whist a second plurality of wall portions of the cartridge are heated by projections 74. This results in the internal cavity of the cartridge in use having a cooled region upstream of a heated region. Thus the gas entering the cartridge 34 at the inlet port 28 is first cooled by the walls of the cartridge 34, promoting condensation of the vapor within the expired gas flow from the patient. In this regard, the gas flow is typically cooled to at or below its due point, such that condensation readily occurs on the internal walls of the cartridge.

Although the cartridge is formed of a generally thin-walled structure, it is noted that the rear wall 44 and/or wall projections 48 which define the recesses in the cartridge are particularly thin walled and may have a wall thickness that is lower than that of the remainder of the cartridge. This is to ensure a low impedance to heat transfer from the gas flow to/from the base unit projections 70, 74.

Once the gas flow passes the final cooled internal wall projection in the cartridge, the gas then enters heated flow passages defined by the downstream internal cartridge walls that are heated by the base unit heater projections 74. Thus heat energy removed from the gas flow by the Peltier device 64 is conducted back to the downstream walls of the cartridge via conductor 72 and projections 74 so as to reheat the gas flow to above its dew point before the gas exits the cartridge via the outlet port. The heat energy imparted back to the gas flow is less than that removed from the gas flow in the condenser. This is controlled by providing a lower surface area for heating than for cooling within the cartridge. Also the provision of the heat dissipating structure within the base unit ensures that a proportion of the heat energy removed from the gas flow is lost to the ambient air. However the partial reheating of the gas flow beneficially reduces the likelihood of subsequent condensation occurring after the gas has exited the cartridge into the conduit 30.

The multiple flow channels caused by the internal baffles within the cartridge 34 provides a large surface area for extracting heat energy from the gas flow. Also the channels within the cartridge 34 define a flow path for the gas such that the heated portion of the cartridge chamber is arranged downstream in flow series from the cooled cartridge portion. This helps to ensure that heat is not transferred to the cooled section by either conduction or else convection.

It has been found that the amount of heat removed from the gas flow by the Peltier device is greater than the amount of heat energy needed to reheat the gas flow to above its dew point. Accordingly the connection between the body 72 on the hot side of the Peltier device and the heat dissipating structure 32 allows excess heat to be lost to the ambient air. Thus the heat dissipating structure acts as a heat sink for the system. The rate of heat loss to ambient air is increased by the airflow caused by fan 58.

It is a notable advantage that the interior of the cartridge 34 is closed from the base unit 32 such that the above described heat transfer functions are achieved within the cartridge 34, whilst avoiding exposure of the remainder of the base unit 32 to the respiratory gas flow. This allows the cartridge 34 to be provided as a replaceable, and typically disposable, component, which can be removed from the base unit 32 after use. The base unit 32 can thus be reused by attaching a new cartridge thereto in the manner described above.

The condensate within the condensing portion of the cartridge interior gathers on the internal walls and runs down to the base wall 39 of the cartridge under the action of gravity. Accordingly a condensate collection arrangement is provided which communicates with the cartridge via the port connector 36 shown in FIG. 2.

Figure 8:
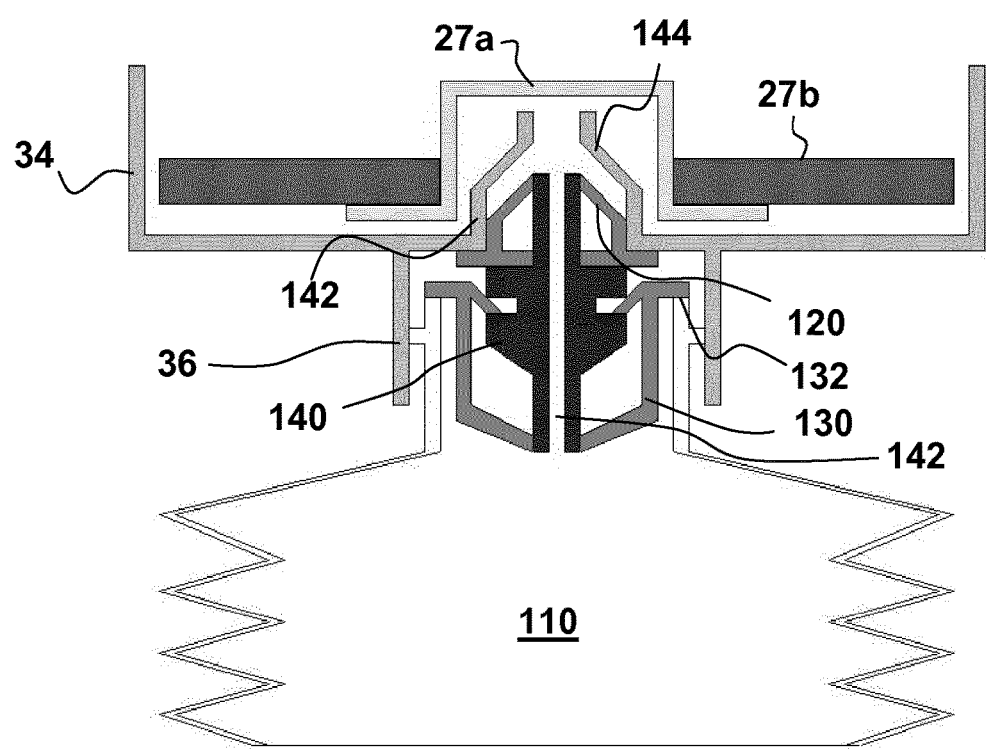
FIG. 8 is a schematic, cross sectional view of collection apparatus for use with the apparatus according to the invention.

One such collection arrangement is shown schematically in FIG. 8. In this arrangement, the base of the cartridge 34 includes an enlarged central aperture 142, and an upstanding spout 144 extends from the central aperture 142 that is closed by the sealing member 27a when the level of water is below the threshold level. Within the central aperture 142 and the liquid drainage port 36, the cartridge 34 is further provided with a valve arrangement that is opened by engagement of a collection vessel 110 with the liquid drainage port 36, and closed by removal of the collection vessel 110.

The valve arrangement comprises an upper duckbill valve 120, a lower duckbill valve 130, and a central connection member 140. The lower duckbill valve 130 includes an outwardly projecting flange 132 that is adapted to be engaged by the upper end of the collection vessel 110, on connection with the liquid drainage port 36, such that the outwardly projecting flange 132 of the lower duckbill valve 130 is urged upwardly. This action causes the lower duckbill valve 130 to be opened. In addition, this action causes the central connection member 140 to be moved upwardly, causing the upper duckbill valve 120 to open. The open configurations of the upper and lower duckbill valves 120, 130 define an outlet passageway 142 from the interior of the upstanding spout 144, into the liquid drainage port 36 and the collection vessel 110.

In this embodiment, the collection vessel 110 is adapted to connect to the liquid drainage port 36 by means of a bayonet connection. In addition, the collection vessel 110 has a bellows structure, such that the collection vessel 110 may be substantially evacuated before use, and expand during use as water condensate collects in the vessel 110.

Figure 9:
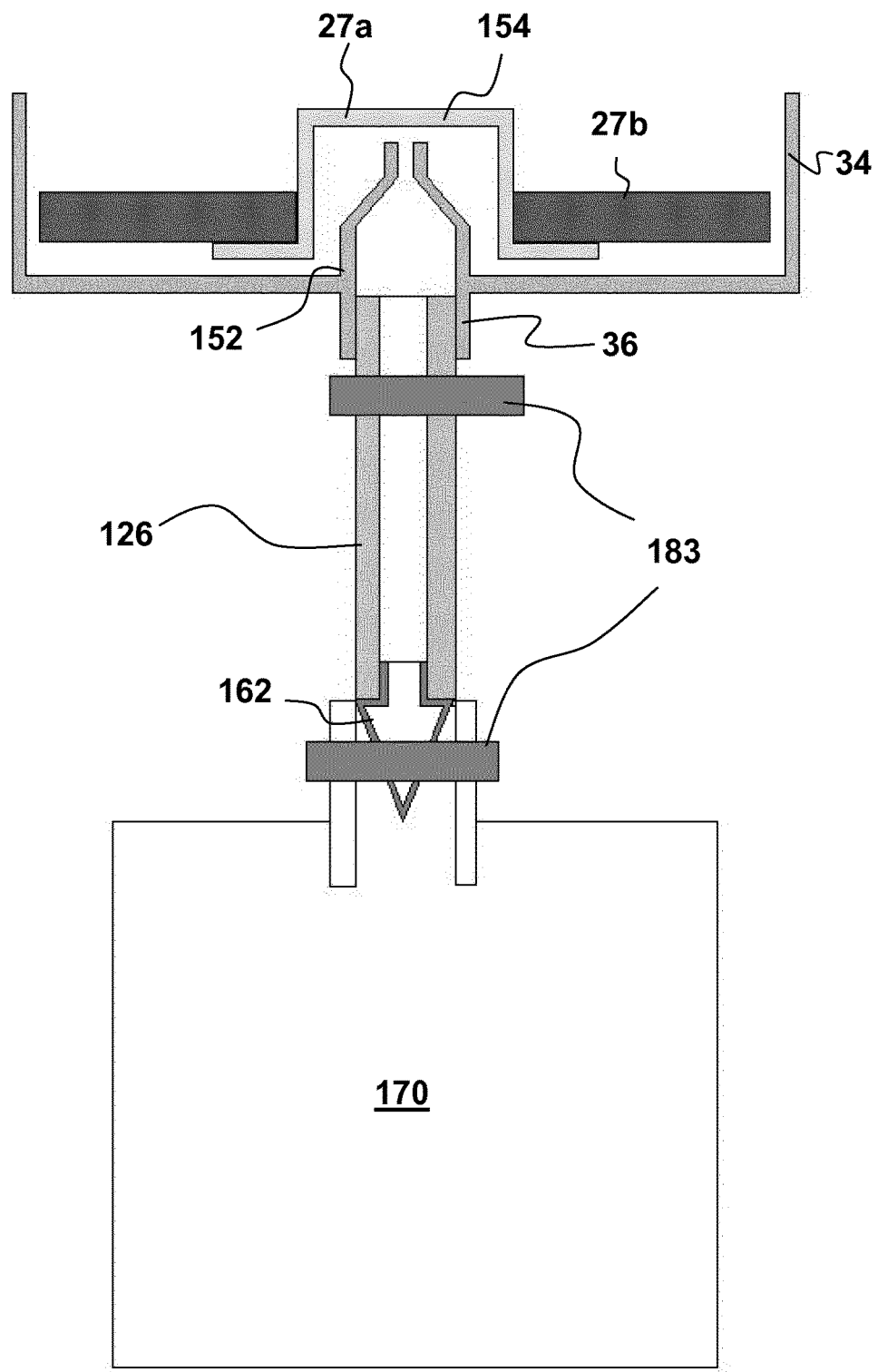
FIG. 9 is a schematic, cross sectional view of alternative collection apparatus for use with the apparatus according to the invention.

An alternative collection arrangement is shown schematically in FIG. 9. In this arrangement, the base of the cartridge 34 again includes an enlarged central aperture 152, and an upstanding spout 154 extending from the central aperture 152 that is closed by the sealing member 27a when the level of water is below the threshold level. In this arrangement, however, the liquid drainage port 36 has a reduced diameter, and is adapted to be connected to one end of a length of small bore tubing 160 that is conventionally using to deliver fluids in medical apparatus. The small bore tubing 160 is connected at its other end to a collection bag 170, within which water condensate is collected. A tube clamp 180 is provided at each end of the small bore tubing 160, which enables the tubing 160 to be closed when replacing the collection bag 170. Otherwise, the small bore tubing 160 remains open during use. A duckbill valve 162 is also provided within the end of the small bore tubing 160 that is connected to the collection bag 170.

The apparatus described above would be constructed with the base unit 32 being housed within a casing (not shown in the Figures). The casing would include an arrangement for releasably engaging the cartridge 34. In particular, the projections 70,74 of the conductor arrangement would be exposed, such that the cartridge 34 may be replaceably engaged with those projections 70,74. The casing would also include flow outlets for the air emitted by the fan 58 to exit the apparatus.

Figure 10:
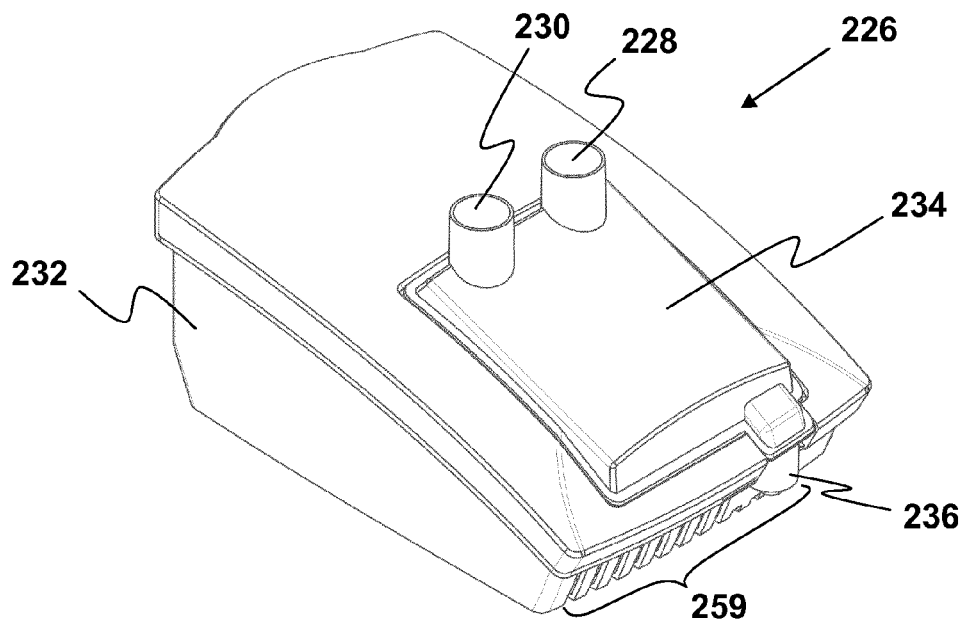
FIG. 10 is a three-dimensional view from the front of a second embodiment of heat exchange apparatus according to the invention.

FIG. 10 shows a second embodiment of dehumidification apparatus according to the invention, which is generally designated 226. The apparatus 226 is similar to the first embodiment described above. However, in this embodiment, the base unit 232 is shown with a casing, which houses an arrangement that is almost identical to the base unit 32 described above in relation to the first embodiment 26, and hence including a heat exchange device (Peltier device), an associated conductor arrangement, a fan unit and an associated heat sink.

The principal difference between the base unit 232 of the second embodiment and that of the first embodiment is that the base unit 232 is provided with a number of projections 274 that are in communication with the hot side of the heat exchange device (Peltier device) that is equal to the number of projections 270 that are in communication with the cold side of the heat exchange device (Peltier device). These projections 270,274 are visible in FIG. 11.

Figure 11:
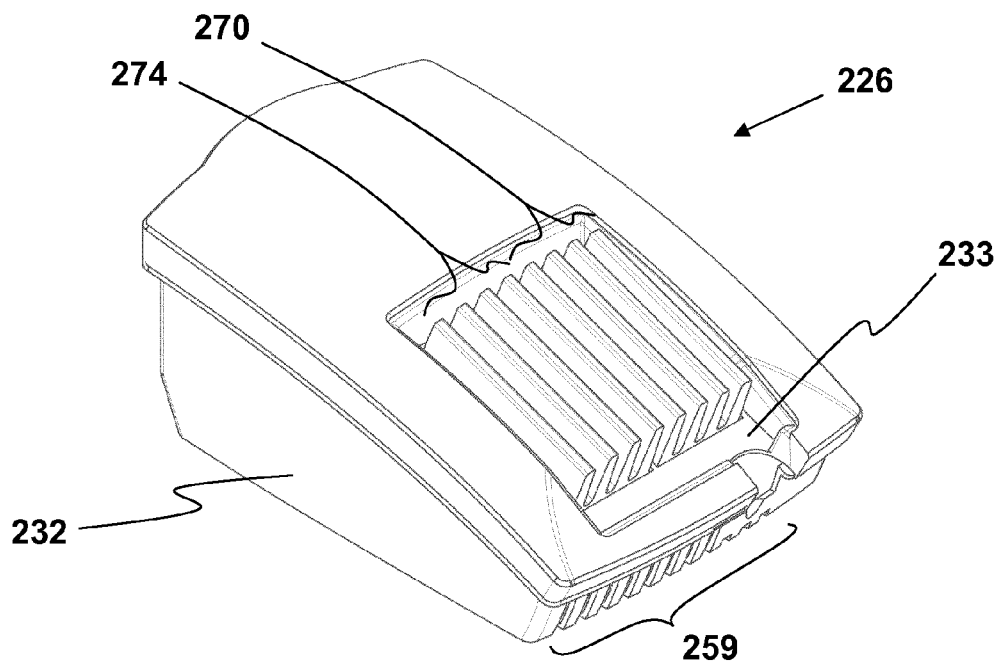
FIG. 11 is a three-dimensional view from the front of the base unit of the apparatus of FIG. 10.

As shown in FIG. 11, the base unit 232 includes a generally rectangular recess 233, of substantially uniform depth, in its upper wall for receiving the cartridge 234. The two sets of projections 270,274 that are in communication with the heat exchange device (Peltier device) 270,274 project from respective openings in the floor of the recess 233, such that these projections 270,274 are upstanding within the recess 233. The recess 233 is arranged at an oblique angle relative to the surface on which the base unit 232 rests, such that the cartridge 234 is arranged at an oblique angle relative to horizontal, in use, and water drains down to the liquid drainage port 236.

The base unit 232 also includes a series of parallel, rectangular openings on its front wall, which serve as outlets for the airflow generated by the fan of the base unit 232.

Figure 12:
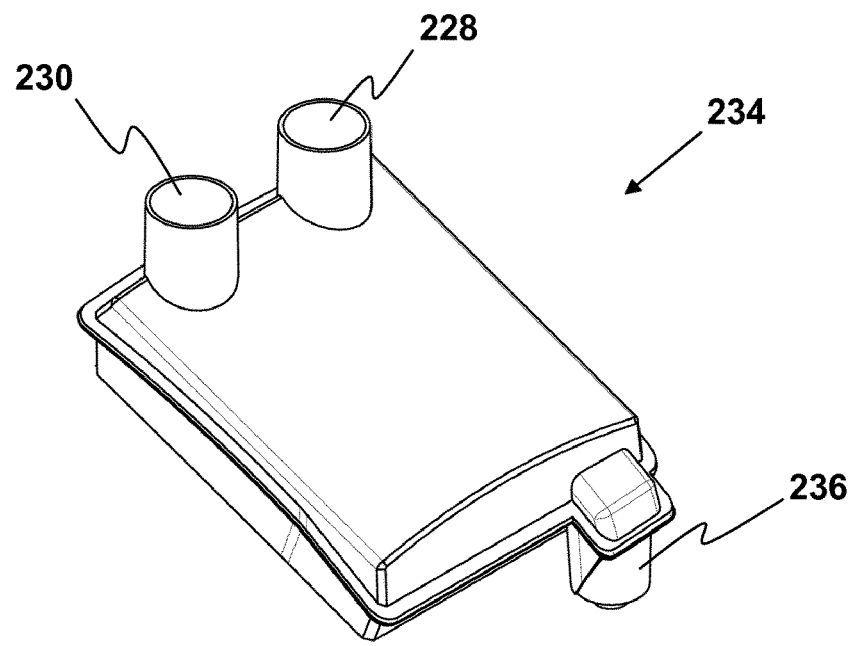
FIG. 12 is a three-dimensional view from above the cartridge of the apparatus of FIG. 10.
Figure 13:
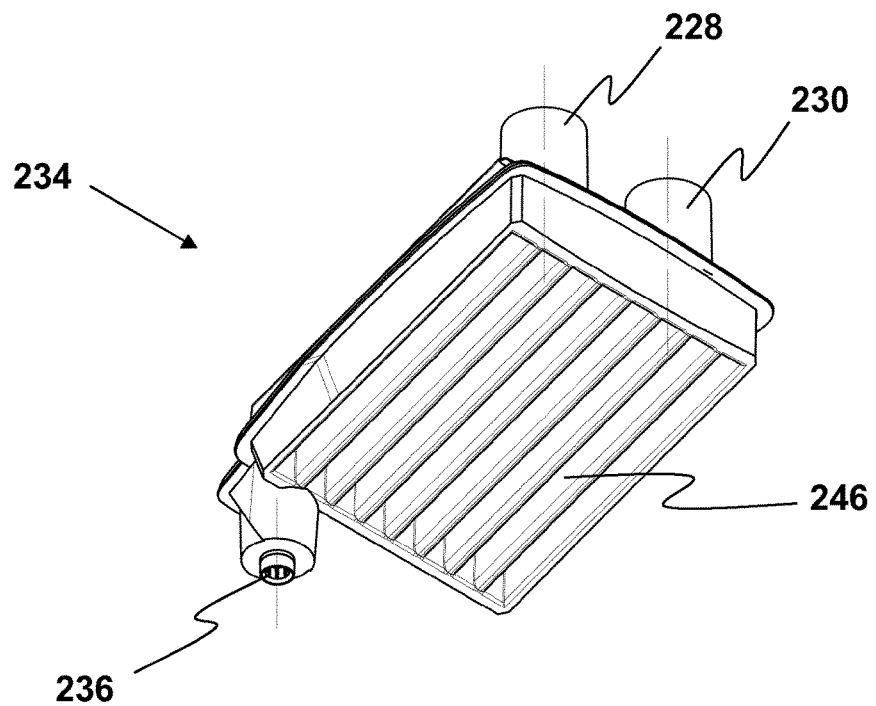
FIG. 13 is a three-dimensional view from below the cartridge of the apparatus of FIG. 10.

As shown in FIGS. 12 and 13, the cartridge 234 is formed of two injection moulded components, which define a flow chamber extending between an inlet port 228 and an outlet port 230. The inlet and outlet port 228 and 230 extend parallel to each other, from one end of an upper surface of the cartridge 234, such that these ports project upwardly from the apparatus 226 when the cartridge 234 is engaged with the base unit 232. At the other end of the cartridge 234, a liquid drainage port 236 extends in the opposite direction to the inlet and outlet ports 228,230, such that the liquid drainage port 236 extends downwardly at one end of the base unit 232, when the when the cartridge 234 is engaged with the base unit 232.

The lower wall of the cartridge, which is visible in FIG. 13, is formed with a plurality of parallel recesses 246, which in turn causes the flow chamber to include a plurality of respective projections. These recesses 246 correspond in number, namely eight, and to the number of projections 270,274 in the recess 233 in the upper wall of the base unit 232, and have a corresponding form, such that these recesses 246 receive the projections 270,274, with a close fit, when the cartridge is engaged with the recess 233. In particular, the exterior surface of the lower wall of the cartridge 234 having these recesses 246 is in contact with the external surface of the projections 270,274 of the base unit 232 to enable effective heat transfer between the cartridge 234 and the base unit 232.

As discussed above, the two sets of projections 270,274 that are in communication with the heat exchange device (Peltier device) 270,274 project from respective openings in the floor of the recess 233, and contact the lower wall of the cartridge 234. Each set of projections 270,274 consists of four parallel projections 270,274, which engage with respective halves of the lower wall of the cartridge 234. In particular, the projections 270 that are in communication with the cold side of the heat exchange device (Peltier device) are in contact with the half of the cartridge 234 into which the inlet port 228 extends, and the projections 274 that are in communication with the hot side of the heat exchange device (Peltier device) are in contact with the half of the cartridge 234 into which the outlet port 230 extends. In this arrangement, as in the arrangement of the first embodiment, the respiratory gases entering the cartridge through the inlet port 228 are firstly cooled by heat transfer to the 'cold' set of projections 270, through the lower wall of the cartridge 234, thereby causing water to condense and flow down to the liquid drainage port. The respiratory gases then pass into the other half of the cartridge 234, and are heated by heat transfer from the 'hot' set of projections 270, through the lower wall of the cartridge 234, such that water no longer condenses. The respiratory gases then exit the cartridge 234 through the outlet 230.

The invention claimed is:

1. A heat exchange apparatus for condensing water from a flow of respiratory gas, the apparatus comprising:
a base unit comprising a heating element and a cooling element, and
a heat exchange component having a condensation chamber, a heater chamber, and a self-contained gases passageway extending from an inlet in fluid communication with the condensation chamber to an outlet in fluid communication with the heater chamber, with the inlet and outlet being connectable to a breathing system such that the condensation chamber and heater chamber are arranged in flow series between the inlet and outlet,
wherein the heat exchange component is releasably engageable with the base unit, such that the heat exchange component is replaceable, and
upon releasably engaging the base unit to the heat exchange component, the condensation chamber is placed in thermal communication with the cooling element to aid removal of heat energy from the condensation chamber and the heater chamber is placed in thermal communication with the heating element to aid provision of heat energy to the heater chamber.

2. Heat exchange apparatus as claimed in claim 1, wherein the heater chamber is adapted to raise a temperature of the respiratory gas flow, in use, to a temperature greater than its dew point prior to the outlet.

3. Heat exchange apparatus as claimed in claim 1, wherein the condensation chamber is arranged to reduce a temperature of the respiratory gas flow downstream of the inlet, and upstream of the heater chamber.

4. Heat exchange apparatus as claimed in claim 1, wherein a temperature of the respiratory gas passing to the outlet is greater than a temperature of the respiratory gas in the condensation chamber.

5. Heat exchange apparatus as claimed in claim 1, wherein the condensation chamber is arranged to reduce the temperature of the respiratory gas flow, in use, to a temperature less than or equal to its dew point, and the heater chamber is adapted to raise the temperature of the respiratory gas flow, in use, to a temperature greater than its dew point.

6. Heat exchange apparatus as claimed in claim 1, wherein the condensation chamber and the heater chamber comprise different regions of a common chamber or enclosure.

7. Heat exchange apparatus as claimed in claim 6, wherein the condensation chamber and the heater chamber are provided within a common housing.

8. Heat exchange apparatus as claimed in claim 1, wherein the base unit comprises a thermoelectric member.

9. Heat exchange apparatus as claimed in claim 8, wherein the thermoelectric member is connectable to a power source, such that it is arranged to drive heat transfer from the cooling element to the heating element.

10. Heat exchange apparatus as claimed in claim 8, wherein the condensation chamber contacts a cold side of the thermoelectric member and the heater chamber contacts a hot side of the thermoelectric member.

11. Heat exchange apparatus as claimed in claim 1, wherein the heat exchange component comprises heat exchange members arranged to protrude into the path of the flow through the apparatus.

12. Heat exchange apparatus as claimed in claim 11, wherein the heat exchange members comprise one or more upstanding walls arranged to define one or more flow passages through the condensation chamber and the heater chamber.

13. Heat exchange apparatus as claimed in claim 12, wherein the upstanding walls further comprise baffles which are arranged so as to define a tortuous flow path through the condensation chamber and the heater chamber.

14. Heat exchange apparatus as claimed in claim 1, wherein the apparatus includes a heat sink for removing excess heat from the apparatus.

15. Heat exchange apparatus as claimed in claim 1, wherein the apparatus includes an arrangement for collection and/or removal of the water condensate from the breathing system comprising an enlarged central aperture and an upstanding spout which extends from the central aperture.

16. A breathing circuit, which includes at least a ventilator or an anesthesia machine, an inspiratory limb, an expiratory limb, and the heat exchange apparatus according to claim 1.

17. A breathing circuit as claimed in claim 16, wherein the heat exchange apparatus is connected within the breathing circuit, such that it forms part of the expiratory limb.

18. A breathing circuit as claimed in claim 17, wherein the expiratory limb comprises at least two breathing tubes, with the heat exchange apparatus connected between the at least two breathing tubes.

19. A base unit for use with a replaceable heat exchange component for condensing water from respiratory gases, the base unit being releasably engageable with the heat exchange component, and the base unit comprising a heat exchange device having a first surface area divided into a cold side and a hot side, wherein the base unit comprises a recess for receiving the heat exchange component and the first surface area is present within the recess, wherein upon releasably engaging the base unit to the heat exchange component the cold side is placed in thermal contact with a first portion of the heat exchange component and the hot side is placed in thermal contact with a second portion of the heat exchange component.

20. A base unit as claimed in claim 19, wherein the base unit comprises a power supply for the heat exchange device.

* * * * *